United States Patent [19]

Sarnoff et al.

[11] Patent Number: 5,102,393
[45] Date of Patent: Apr. 7, 1992

[54] AUTOINJECTOR CONVERTED FROM INTRAMUSCULAR TO SUBCUTANEOUS MODE OF INJECTION

[75] Inventors: Stanley J. Sarnoff, Bethesda; Claudio Lopez, Gaithersburg, both of Md.

[73] Assignee: Survival Technology, Inc., Bethesda, Md.

[21] Appl. No.: 380,451

[22] Filed: Jul. 17, 1989

[51] Int. Cl.⁵ .............................................. A61M 5/20
[52] U.S. Cl. .................................. 604/136; 604/117; 604/135; 604/134
[58] Field of Search ............... 604/130, 134, 136, 187, 604/194, 197–198, 201, 218, 192, 117, 220, 263, 135, 137–139, 157

[56] References Cited

U.S. PATENT DOCUMENTS

| | | |
|---|---|---|
| 1,767,304 | 6/1930 | Morton . |
| 2,704,072 | 3/1955 | Sarnoff . |
| 2,832,339 | 4/1958 | Sarnoff et al. . |
| 3,136,313 | 6/1964 | Enstrom et al. . |
| 3,368,558 | 2/1968 | Sarnoff et al. . |
| 3,380,449 | 4/1968 | Sarnoff . |
| 3,391,695 | 7/1968 | Sarnoff . |
| 3,396,726 | 8/1968 | Sarnoff . |
| 3,403,679 | 10/1968 | Sinclair et al. ............... 604/138 |
| 3,795,061 | 3/1974 | Sarnoff et al. . |
| 3,882,863 | 5/1975 | Sarnoff et al. . |
| 3,910,260 | 10/1975 | Sarnoff et al. . |
| 4,004,577 | 1/1977 | Sarnoff . |
| 4,031,893 | 6/1977 | Kaplan et al. . |
| 4,270,537 | 1/1981 | Romaine ........................ 604/117 |
| 4,316,463 | 2/1982 | Schmitz et al. ................ 604/130 |
| 4,373,526 | 2/1983 | Kling ............................. 604/198 |
| 4,592,745 | 6/1986 | Rex et al. ....................... 604/192 |
| 4,689,042 | 8/1987 | Sarnoff et al. . |
| 4,755,169 | 7/1988 | Sarnoff et al. . |
| 4,795,433 | 1/1989 | Sarnoff . |

FOREIGN PATENT DOCUMENTS

| | | |
|---|---|---|
| 0186916 | 7/1986 | European Pat. Off. ............ 604/136 |
| 0180761 | 1/1955 | Fed. Rep. of Germany ...... 604/192 |

OTHER PUBLICATIONS

American Heritage Dictionary 2nd College Edition Houghton Mifflin Co. 1982, pp. 633 and 1211 (hypodermic Subcutaneous).

*Primary Examiner*—Stephen C. Pellegrino
*Assistant Examiner*—Michael Rafa
*Attorney, Agent, or Firm*—Cushman, Darby & Cushman

[57] ABSTRACT

An autoinjector converted from an intramuscular to a subcutaneous mode of injection comprising a housing having a medicament cartridge assembly mounted within the housing means in a storage position for movement out of the storage position and a releasable stressed spring assembly for moving the medicament cartridge assembly means out of the storage position. The stressed spring assembly is operable in response to a manual actuating procedure which does not require compression of the subcutaneous tissue to effect an intramuscular mode of injection by moving the hypodermic needle of the cartridge assembly outwardly of the housing into the muscle tissue at the injection site of a user and a major portion of the liquid medicament of the cartridge assembly outwardly through the hypodermic needle into the muscle tissue of the user. An injection mode converting structure is secured in a subcutaneous mode position for converting the mode of injection effected by the stressed spring assembly from the intramuscular mode of injection to a subcutaneous mode of injection in which the needle cannot extend substantially beyond subcutaneous tissue at the injection site of the user and a major portion of the liquid medicament enters into the subcutaneous tissue.

22 Claims, 2 Drawing Sheets

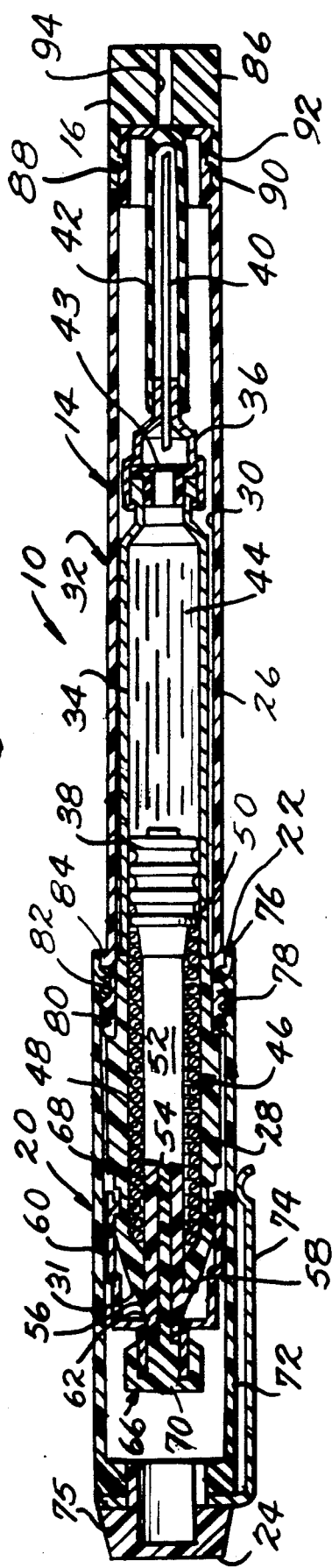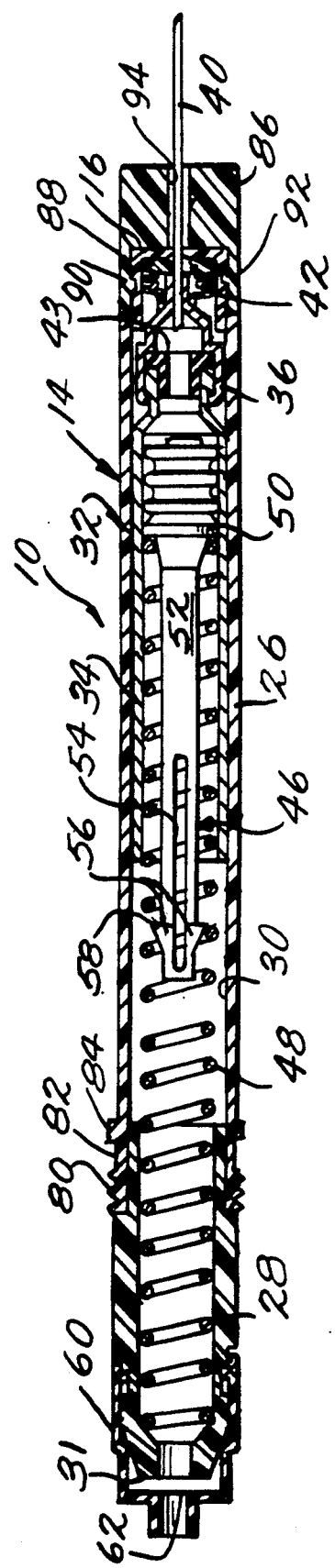

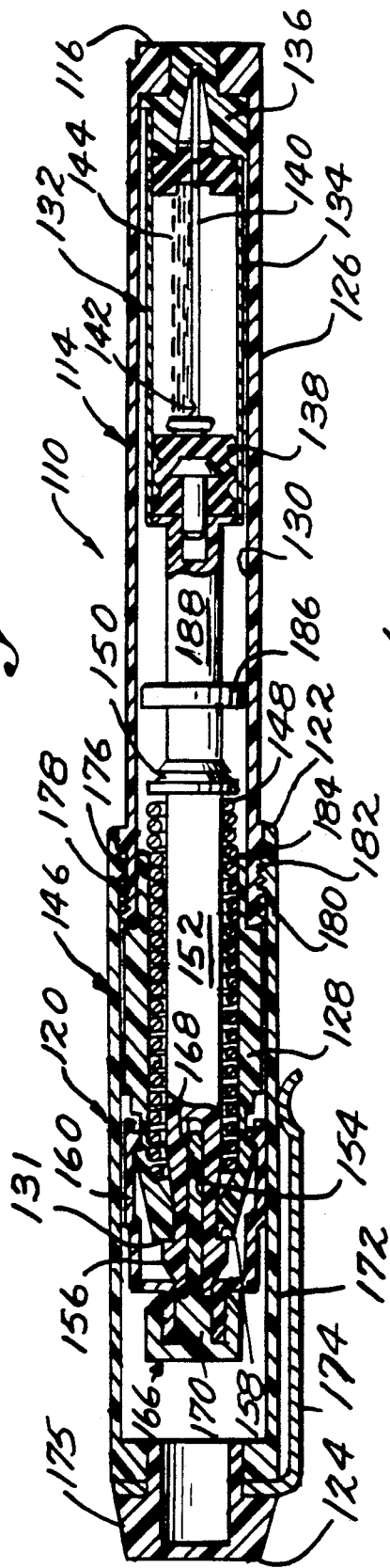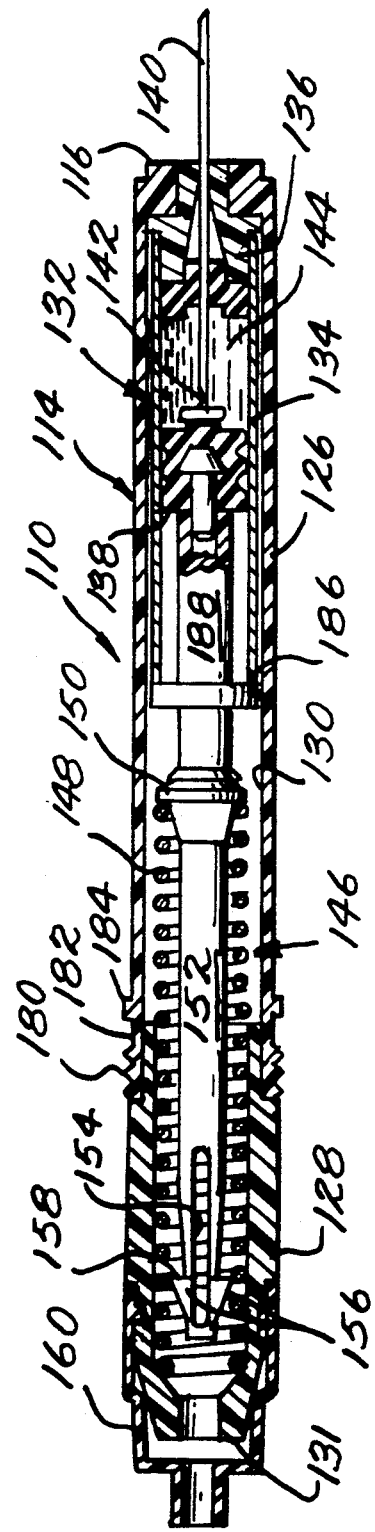

AUTOINJECTOR CONVERTED FROM INTRAMUSCULAR TO SUBCUTANEOUS MODE OF INJECTION

This application relates to devices for injecting liquid medicaments and, more particularly, automatic injector types of such devices.

Automatic injectors are well known. Basically, an automatic injector is a device for enabling an individual to self-administer a dosage of a liquid medicament. An advantage of automatic injectors is that they contain a measured dosage of a liquid medicament in a sealed sterile condition capable of storage in such condition for an extensive period of non-use, during which period immediate injection of the stored dosage may be accomplished at any time under the most severe emergency conditions. Another advantage of automatic injectors is that the administration of the self-contained dosage of liquid medicament is accomplished without the necessity of the user initially seeing the hypodermic needle through which the liquid medicament is injected or of manually penetrating such a visible needle into the user's own tissue. Instead, an automatic injector includes a releasable stressed spring assembly. This assembly includes a stressed spring, a releasable mechanism for releasably retaining the spring in a stressed storage position and a releasing mechanism for releasing the releasable mechanism in response to a predetermined actuating procedure.

Automatic injectors have heretofore been particularly suited for use under emergency conditions. For example, many tens of millions of such automatic injectors have been manufactured and sold containing nerve gas antidotes for use under emergency chemical warfare conditions. Typical units which have been utilized for this purpose are disclosed in U.S. Pat. Nos. 2,832,339, 3,882,863, and 4,031,893. In addition, units of this type have been proposed for use in administering antiarrhythmic medicaments under emergency conditions relating to heart attack medical situations. Such use has been in conjunction with portable monitors as is evident from the disclosure contained in U.S. Pat. Nos. 3,910,260 and 4,004,577. It has also been proposed to provide other medicaments useful in treating heart attack symptoms such as clot selective thrombolytic agents (e.g. tPA) and related medicaments. See, for example, U.S. Pat. Nos. 4,689,042, 4,755,169, and 4,795,433. Finally, automatic injectors have been marketed in recent years containing a dosage of epinephrine as an antidote for counteracting severe allergic reactions, as for example, to bee stings and the like.

In all of these instances, the emergency use aspect of the automatic injectors is of primary significance. Moreover, in all of these instances the autoinjector is specifically structured so that in its normal operation, the needle extends into the muscle tissue of the user and a major amount if not all of the liquid medicament is injected into the muscle tissue of the user. However, in the case of the epinephrine autoinjector, it is suggested that subcutaneous operation can be elected by canting the injector with respect to the skin rather than maintaining it perpendicular in the normal operating mode. By effecting actuation following the canting movement, it becomes possible to keep the needle extension within the subcutaneous tissue and to insure that a major amount if not all of the liquid medicament is injected into the subcutaneous tissue of the user.

In commonly assigned patent application, Ser. No. 380,459 filed 07/19/99, there is recognition that the advantages of automatic injectors are not limited only to emergency situations but that there are many other medicinal administration situations requiring a much more frequent usage where the painlessness and simplicity of actuation of an automatic injector combined with other conveniences, would be sufficiently desirable to many individuals to warrant the added costs in comparison with the more simple and less costly manual syringes in widespread use. An example given in the disclosure is the drug erythropoietin recently approved by the FDA in combating anemia. The drug is particularly useful to kidney patients, aids patients, and patients donating blood for their own use in anticipation of elective surgery. Such patients may have need for the administration of erythropoietin as frequently as once a week. An automatic injector provides a very convenient way of allowing the patient to administer the necessary erythropoietin without requiring the patient to become proficient in inserting a needle into his own flesh.

The present invention stems from the further recognition that in some of these more frequent and less emergency type situations where convenience assumes a much more important role, as well as in some future emergency situations, a subcutaneous operational mode of injection may be indicated by the nature of the FDA approval, such as in the case of erythropoietin, therefore making it highly desirable, if not essential, to construct the autoinjector so that only a subcutaneous operating mode can be achieved. The present invention stems from the further recognition that it is desirable from a cost effectiveness standpoint to convert autoinjectors operating in an intramuscular mode of injection into a subcutaneous mode of injection rather than to make a line of injectors specifically designed for operation in a subcutaneous mode of injection in addition to the line of injectors operating in an intramuscular mode of injection. Such cost effectiveness can particularly be realized if conversion can be accomplished by simply securing a separate structure in a subcutaneous mode position with respect to the autoinjectors.

The present invention is also based upon the observation that the mode of actuation of an autoinjector can have an effect on its capability to operate effectively in a subcutaneous mode of injection. All of the autoinjectors described above have a mode of actuation in which the manual actuating procedure involves the user gripping the outer tube of the autoinjector and then pushing the forward end of the housing into the skin at the injection site. The pushing action must be under a pressure to cause a relative movement to occur between the forward end of the housing and the outer tube which is sufficient to cam the flexible locking wedge portions of the collet out of spring pressed locking relation with the locking surfaces engaged thereby. The extent of the pushing action required is sufficient to apply a significant compressive force to the skin, the result of which was often a compression of the subcutaneous tissue to an extent sufficient to permit needle penetration beyond the boundary between the subcutaneous tissue and the muscle tissue. The effect of this subcutaneous tissue compression by the actuation procedure to the tissue location of the liquid medicament itself after injection is particularly significant in the type of autoinjector where the liquid medicament moves out of the needle while the needle is moved into the tissue (e.g. 2,832,339) as compared with those where the liquid medicament is moved out of the needle only after the penetrating movement of the needle is over (e.g. 3,882,863). In the first instance, the situs of the liquid medicament is dispersed between (1) the relatively short penetration position of the needle and where liquid medicament entry begins and (2) the final relatively long penetration position of the needle end where liquid medicament entry ends. In the second instance, the situs of the liquid medicament is concentrated, in the final penetration position. In the first instance, because of the depth dispersal of the medicament situs, the subcutaneous tissue compression obtained by the actuation mode was often required in order to insure that a major portion of the liquid medicament was actually delivered to the muscle tissue. Thus, the amount of liquid medicament actually delivered to the subcutaneous tissue was a function of the thickness or depth of the compressed subcutaneous tissue and the position of penetration where flow of liquid medicament through the needle end commenced. The latter characteristic is determined by the amount of gas which is placed within the medicament cartridge container along with the liquid medicament dosage therein and the extent of travel of the container piston in order to get the needle end from its storage position into a position to begin skin penetration. These factors are discussed in detail in U.S. Pat. No. 3,396,726, the disclosure of which is hereby incorporated by reference into the present specification. All of these considerations and particularly the necessity to compress the subcutaneous tissue to accomplish actuation, makes this type of actuation unsuitable for an autoinjector which can be converted from an intramuscular mode of injection to a subcutaneous mode of injection wherein a major portion of the liquid medicament is to be delivered to the subcutaneous tissue. In accordance with the principles of the present invention, the autoinjector of the present invention should have the capability of being actuated in operative relation with the skin at the injection site of the user in such a way as to cause no compression of the subcutaneous tissue under the skin. This actuation capability is particularly for the subcutaneous mode of injection of the autoinjector. For the intramuscular mode, it may be desirable to have the operative relationship between the autoinjector housing and the skin one in which the subcutaneous tissue is compressed. Consequently, it is desirable that the actuating procedure be one in which the housing is manually held in the desired operating relation either compressing or non-compressing while actuation is effected digitally.

In accordance with the principles of the present invention, this recognized cost effectiveness is achieved by providing an autoinjector converted from an intramuscular to a subcutaneous mode of injection comprising a housing assembly, a medicament cartridge assembly mounted within the outer housing assembly in a storage position for movement out of the storage position, and a cartridge moving assembly carried by the housing assembly for moving the medicament cartridge assembly out of the storage position. The medicament cartridge assembly includes a container, a hypodermic needle and a medicament disposed in a storage condition within the container means when the medicament cartridge assembly means in the storage position operable when the medicament cartridge assembly is moved out of the storage position to provide liquid medicament injectable through the hypodermic needle. The cartridge moving assembly constitutes a stressed spring assembly for effecting an intramuscular mode of injection by moving the hypodermic needle outwardly of the housing assembly into the muscle tissue at the injection site of a user and a major portion of the liquid medicament outwardly through the hypodermic needle means into the muscle tissue of the user. The stressed spring assembly means includes spring means, releasable means for releasably retaining the spring means in a stressed condition, and releasing means for releasing the releasable means in response to the performance of a predetermined manual actuating procedure which includes a digital actuation while holding the housing means in an operative relation with respect to the skin at the injection site of the user, which may be such as to cause no compression of the subcutaneous tissue under the skin. A separate structure is provided which is secured in a subcutaneous mode position for converting the mode of injection effected by the stressed spring assembly from the intramuscular mode of injection to a subcutaneous mode of injection in which the needle cannot extend substantially beyond subcutaneous tissue at the injection site of the user during the movement of the needle outwardly of the housing means and a major portion of the liquid medicament enters into the subcutaneous tissue of the user during the movement of the liquid medicament outwardly of the needle.

Another object of the present invention is the provision of an autoinjector of the type described which is simple in construction, effective in operation and economical to manufacture.

These and other objects of the present invention will become more apparent during the course of the following detailed description and appended claims.

The invention may best be understood with reference to the accompanying drawings wherein illustrative embodiments are shown.

IN THE DRAWINGS

FIG. 1 is a longitudinal sectional view of one embodiment of an autoinjector embodying the principles of the present invention showing the same in its storage position;

FIG. 2 is a view similar to FIG. 1 showing the autoinjector in the position assumed after injection;

FIG. 3 is a view similar to FIG. 1 showing another embodiment of an autoinjector embodying the principles of the present invention; and FIG. 4 is a view similar to FIG. 2 of the autoinjector shown in FIG. 3.

Referring now more particularly to FIGS. 1 and 2 of the drawings, there is shown therein an autoinjector or automatic injector device, generally indicated at 10, which embodies the principles of the present invention. While the principles of the present invention have applicability to any known autoinjector construction, a preferred construction is the conveniently carried frequent use autoinjector such as disclosed in the aforesaid patent application Ser. No. 380,459 filed 07/19/89 previously cited. The autoinjector 10 presents an exterior configuration which is of a size approximately the same as that of a conventional fountain pen. The forward exterior is defined by a housing body assembly, generally indicated at 14, of elongated generally cylindrical configuration providing a forward needle extension end 16. The rearward exterior of the device is defined by a separate housing cap structure, generally indicated at 20, which is of elongated generally cylindrical configuration having an open end 22 and an opposite closed end 24.

The housing body assembly 14 includes two fixed forward and rearward tubular housing members 26 and 28, respectively. The forward housing member 26 is of greater length and provides the forward needle extension end 16 of the housing body assembly 14. The two fixed housing members together define an interior chamber 30 extending from the forward end 16 of the forward member 26 to a rearward end 31 of the rearward member 28. Mounted in a storage position within the needle extension end 16 of the chamber 30 provided by the forward housing member 26 is a medicament cartridge assembly, generally indicated at 32. The assembly 32 includes a generally cylindrical medicament container 34 which is open at its rearward end and necked down at its forward end to receive a hub assembly 36. A piston 38 closes the open rearward end of the container 34 and is mounted therein for forward sliding movement in sealing relation with the interior of the container 34. The hub assembly 36 has fixed to the forward end thereof the rearward end of a hypodermic needle 40 which extends forwardly therefrom. The hypodermic needle 40 and the hub structure 36 is encased within a resilient sheath 42. Preferably, as shown, the hub assembly 36 is of the type which includes a burstable seal 43 in the rearward portion thereof, such as disclosed in U.S. Pat. No. 3,380,449 and 3,391,695, the disclosures of which are hereby incorporated by reference into the present specification. The seal 43 of the hub assembly 36 serves to sealingly confine a liquid medicament 44 within the container 34 at its forward end with the piston 38 confining it at its rearward end.

A releasable stressed spring assembly, generally indicated at 46, is carried by the rearward housing member 28. It is preferable to assemble the components of the stressed spring assembly 26 with the rearward housing member 28 prior to the connection of the two housing members 26 and 28 together. Consequently, the housing member 28 may also be considered a part of the stressed spring assembly 46 as well as a part of the housing body assembly. In this regard, it will be noted that the forward end of the rearward housing member 28 is of reduced diameter so as to engage within the hollow rearward end of the forward housing member 26. The engagement preferably is fixed either by sonic welding adhesive, press fit or other means such as threads, etc.

The stressed spring assembly 46 includes a compression coil spring 48 within the chamber 30 which has one end engaged within the interior of the opposite end 31 provided by the rearward housing member 28. The opposite end of the spring 48 is stressed against an annular flange 50 formed on a forward end of a collet 52 which constitutes a releasable mechanism for retaining the spring 48 in stressed condition. The collet 52 may be of any conventional configuration, however, as shown, it is constructed of plastic material in the manner disclosed in U.S. Pat. No. 3,795,061, the disclosure of which is hereby incorporated by reference into the present specification. As shown, the collet is hollow and has its rearward end divided, as by a slot 54 into two flexible portions. Formed on the rearward end of the flexible portions are arcuate locking wedges 56 having forwardly facing locking surfaces 58 which engage the rearwardly facing annular surface provided by the opposite end 31 of the rearward housing member 28.

The stressed spring assembly 46 also includes a releasing mechanism which is in the form of a tubular releasing member 60. The releasing member 60, as shown, extends over the rearward end of the rearward housing member 28 and extends forwardly for a short distance in surrounding relation to the rearward housing member 28 so as to define a rearward portion of the exterior of the device when the cap structure 20 is removed. Accordingly, the member 60 may also be considered part of the housing assembly 14 even though it constitutes a part of the stressed spring assembly 46. In this regard, it is similar to the housing member 20 in that it too forms a part of both the housing assembly 14 and the stressed spring assembly. As shown, the tubular member 60 is mounted for movement between a rearward storage position and a forward actuating position. As shown, the forward end of the tubular releasing member 60 includes a flange or series of spaced projections extending around the interior periphery thereof for seating within an annular groove in the exterior periphery of the rearward housing member 28. The rearward end of the releasing member is of reduced diameter and engages around the cylindrical terminal end of the collet 52 when the releasing member 60 is in its storage position. The reduced end includes a forwardly facing annular surface 62 which is disposed to engage the rearwardly facing segmental frustoconical surfaces of the locking wedges 56.

It can be seen that when the releasing member 60 is moved from its storage position, as shown, forwardly into its actuating position, the forwardly facing annular surface 62 of the releasing member 60 will engage the segmental frustoconical surfaces of the locking wedges 56 causing the locking wedges 56 to move inwardly toward one another, thus moving the locking surfaces 58 of the wedges out of engagement with the rearward surface of the opposite end 31 of the rearward housing member 28, thus enabling the stressed spring 48 acting on the flange 50 of the collet 52 to move the collet 52 forwardly. The flange 50 of the collet 52 and released spring 48 act directly on the piston 38 in such a way as to move the entire medicament cartridge assembly 32 forwardly within the chamber 30 defined by the housing members 26 and 28. During this initial movement, the sharpened forward end of the hypodermic needle 40 pierces the end of the sheath 42 and moves outwardly of the needle extension end 16 of the housing member 26 and into the tissue of the user. As this movement continues, the resilient sheath 36 is compressed so as to ultimately retard and stop the forward movement of the medicament container 34. When the medicament container 34 stops, the penetration of the needle within the user's tissue likewise stops but the piston 38 continues under the action of the spring to move forwardly initially causing the burstable seal 43 to burst and then the liquid medicament 44 to move from within the container 34 through the hypodermic needle 40 and into the tissue of the user.

The stressed spring assembly 46 also includes a safety, generally indicated at 66, which includes a forwardly extending safety pin 68 of a size to engage within the hollow interior of the rearward portion of the collet 52 so as to prevent the two locking wedges 66 to move toward one another. The safety also includes a cap 70 which, as shown, extends rearward from the rearward end of the housing body assembly defined by the releasing member 60. The cap is integrally interconnected with the safety pin 68 by a central enlargement which, in the safety storage position shown, extends within the reduced rearward end of the releasing member 60 in engagement with the end of the collet 52.

A feature of the construction of the autoinjector 10 is that the housing cap structure 20 provides both a convenience to the user in carrying the autoinjector 10 on the person of the user and an added safety factor which prevents the stressed spring assembly 46 from being actuated without removing the housing cap structure 20. To this end, the housing cap 20 structure includes a tubular cap member 72 having fixed thereon a resilient clip 74. The clip 74, as shown, is of L-shaped configuration having one leg formed in a annular configuration so as to be fixed to the rearward end 24 of the housing cap structure 20. In this regard, it will be noted that the cap member 72 is an open ended tubular member and a closure 75 is provided to close the rearward open end thereof. The closure 75 includes a forwardly extending skirt which seats within the open end of the cap member 72 so as to capture the annularly shaped leg of the clip 74 therein. The other leg of the L-shaped clip 74 extends forwardly along the cap member 72 and has a knob formation on its forward extremity which is resiliently biased by the material of the clip 74 to engage the adjacent exterior periphery of the cap member 72. It will be understood that the construction of the cap structure 20 including the clip 74 and the manner of attaching the clip 74 are exemplary only and that other constructions and modes of assembly may be utilized if desired.

The autoinjector 10 is provided with interengaging means between the cap structure 20 and the housing body assembly 14 for detachably securing the cap structure 20 in open ended telescopic relation with respect to the opposite end portion of the housing body assembly, as shown. It is preferable to provide a means which requires for removal a combination of at least two different movements, either sequentially or simultaneously, so as to make the removal of the cap structure 20 from the housing body assembly 14 relatively difficult for children to accomplish. One embodiment of such a means is best shown in FIG. 3 as including a short section of threads 76 on the interior of the cap member adjacent the forward open end 22 thereof with a groove 78 formed inwardly adjacent the threaded section 76. Similarly, the exterior periphery of the rearward end of the rearward housing member 28 is formed with a cooperating exterior thread section 80 and an inwardly adjacent annular groove 82. As shown, a stop flange 84 is provided on the exterior of the housing member 26 so as to define the forward extremity of the groove 82 and capture the thread section 76 of the cap structure 20 therein when in attached relation. It can be seen that the cap structure 20 is attached by simply interengaging the threads 76 with the threads 80 and effecting a relative turning movement between the cap structure 20 and the housing body assembly 14. This turning movement will ultimately result in the interior thread section 76 engaging within the groove 82 and the exterior thread section 80 engaging within the groove 78, as best shown in FIG. 3. This interengagement serves to retain the cap structure 20 on the housing body assembly 14 in such a way that a simple relative turning movement between the cap structure and the body assembly will merely result in the two thread sections rotating within the grooves within which they are engaged. In order to remove the cap structure 20, it is necessary to apply a rearward pulling movement in addition to the turning movement to ensure that the thread sections 76 and 80 will initially interengage and then mesh throughout the turning action until they finally release to permit the cap structure 20 to be removed. It will be understood that other compound movements can be utilized such as a sequential push-in movement and then a turning movement.

The autoinjector as described above is particularly convenient to be carried on the person of a user in a manner similar to a conventional fountain pen. The exterior configuration of the device fits easily within the pocket and the clip 74 serves to retain the housing body assembly 14 and the cap structure 20 in the pocket on the person of the user.

In accordance with the principles of the present invention, the autoinjector 10 is provided with an injection mode converting means for converting the normal intramuscular mode of injection of the autoinjector into a subcutaneous mode of injection. By the provision of such an injection mode converting means, the autoinjector 10 is rendered much more versatile while obtaining all of the advantages of desirable size, shape, appearance and manufacturing cost effectiveness embodied in the construction of the autoinjector 10 irrespective of its use either as a subcutaneous injector or as an intramuscular injector. In FIGS. 1 and 2, the injection mode converting means is shown as being in the form of a tip extension member 86 secured to the needle extension end 16 of the forward housing member 26 in a subcutaneous mode position. As shown, the tip extension member 86 is removably secured in its subcutaneous mode position by a rearwardly extending skirt 88 having an annular ridge 90 on the interior periphery thereof which is adapted to snap into an annular groove 92 formed in the exterior periphery of the forward housing member 26. This snap action securement is sufficient to firmly retain the tip extension in its subcutaneous mode position. While removable securement is preferred, either a movable or a fixed securement may be employed. A movable securement contemplates a retention of the mode converting structure with the autoinjector when moved out of its subcutaneous mode position rather than removal as shown. These two modes of securement may permit manual reconversion if desired. A fixed securement, as for example, by sonic welding, prevents simple manual reconversion. In the subcutaneous mode position forwardly of the forward end 16, the extension member must be constructed to allow movement of the needle 40 therethrough. As shown, the member is molded of a plastic material with a central needle receiving opening 94 therein. The plastic material utilized is suitable to provide sufficient flexibility to the skirt to facilitate the snap action previously described.

Conventional intramuscular autoinjectors have a needle penetration length of approximately 0.8 inches. The depth of the subcutaneous layer varies throughout the body of any individual and the variations vary from individual to individual with the variation being greater between non-adults and adults. Disregarding the latter because more often than not the dosage will be varied to accommodate these variations a typical subcutaneous depth at the injection site where autoinjectors are utilized most often, i.e. the thigh, may be considered to be approximately 0.625 inches in its uncompressed state. Consequently, an exemplary embodiment of the axial dimension of the extension member is approximately 0.3 inches resulting in a needle penetration of 0.5 inches. It will be understood that this 0.5 inch dimension from the forward skin contacting surface of the extension member to the forward skin contacting surface of the forward end 16 of the housing body assembly 14 is exemplary only and can be varied to suit a particular situation.

While it is preferable to utilize a cartridge assembly 32 of the type described above in which medicament flow occurs after needle penetration, the principles of the present invention are also applicable to cartridge assemblies of the type in which flow occurs simultaneously with the penetrating movement of the needle. FIGS. 3 and 4 illustrate an autoinjector 110 which embodies such a medicament cartridge assembly. Since the other components of the autoinjector 110 are similar to the other components of the autoinjector 10 previously described, these other components will not be described in detail but instead they are designated in the drawings by the corresponding reference numeral with the numeral 1 as a prefix thereto. The autoinjector 110 includes a medicament cartridge assembly, generally indicated at 132, which differs from the cartridge assembly 32 in that it includes a container 134 having a forward end closed, as by an elastomeric stopper or plug assembly 136. A piston 138 closes the rearward end of the container 134 and is mounted therein for forward sliding movement in sealing relation with the interior of the container 134.

Mounted within the container 134 between the plug assembly 136 and the movable piston 138 is a hypodermic needle 140 having a forward sharpened end positioned within the plug assembly 136 and a rearward blunt end disposed adjacent the piston 138. A lateral opening 142 is formed adjacent the blunt end of the needle 140 to provide communication through the hollow hypodermic needle 140 of a medicament 144 also stored within the container 134 between the plug assembly 136 and the piston 138. In accordance with conventional practice, the liquid medicament 144 does not completely fill the space defined by the container between the plug assembly 136 and the piston 138, but instead, there is an appropriate amount of air or other gas contained therein all in accordance with the teachings set forth in the aforesaid U.S. Pat. No. 3,396,726.

With respect to the contents of the container 134, the amount of air chosen is interrelated to the amount of the liquid medicament 144 which, in the case of the cartridge assembly 132, is an amount greater than the intended dosage to be injected in the subcutaneous mode. The subcutaneous mode is determined by a separate subcutaneous mode member 186 secured to a spacer 188 disposed between the piston 138 of the cartridge assembly 132 and the collet flange 150 of the stressed spring assembly 146. As shown, the mode member 186 is in the form of a collar press fit or otherwise secured to the spacer in a subcutaneous mode position therein. This position with respect to the housing body assembly 114 when the cartridge assembly is in its storage position is within the forward housing member 126 spaced rearwardly from the rearward edge of the medicament container 134.

The autoinjector 110 like the autoinjector 10 is particularly convenient to be carried on the person of a user in a manner similar to a conventional fountain pen. The exterior configuration of the device fits easily within the pocket and the clip 174 serves to retain the housing body assembly 114 and the cap structure 120 in the pocket on the person of the user. When it is desired to use the autoinjector, the user simply removes the autoinjector 110 from his pocket and utilizing the compound movements previously described removes the cap structure 120. This cap removal may be considered an initial step in a predetermined actuating procedure which must be accomplished in order to administer the medicament 144. The second step is to remove the safety 166 from its storage position by simply digitally gripping the cap 170 and pulling rearwardly with the housing body assembly gripped within the palm of one hand. Next, the thumb of the hand gripping the housing body assembly is extended over the rearward end portion of the releasing member 160. The needle extension end 116 of the housing member 126 is then brought into non-pressure contact with the user's skin in the area where it is desired to effect the injection of the medicament. Once this non-pressure contact has been established and held, the user simply presses his thumb down on the rearward end of the releasing member 160 which has the effect of moving the locking wedges 156 inwardly towards one another, releasing the spring 148 and thus moving the spacer 188 and mode member 186 forwardly. Movement of the spacer 188 forwardly carries with it the piston 138 and the needle 140. This joint movement continues until the mode member 186 engages the rearward end of the container 134 at which time all movement stops. During an initial portion of the movement of the piston 138 and needle 140 together, the air within the container is compressed while the sharpened end of the needle passes through the plug assembly 136 and into the skin. After penetrating the skin further movements results in flow of the liquid medicament out of the needle into the subcutaneous tissue of the user. As before, the actual penetration of the needle 140 is approximately 0.5 inches which is within the aforesaid dimension of 0.625 inches of non-compresses subcutaneous tissue thickness. In the absence of the subcutaneous mode member 186 with the autoinjector 110 in an intramuscular mode, the needle would penetrate 0.8 inches into the injection site with the subcutaneous tissue compressed (by holding the housing with some inward pressure) so that the major portion of the liquid medicament would enter the muscle tissue.

While a stressed spring assembly having a separate safety member which is removable and which requires an additional actuating step to effect actuation after safety removal is shown, it will be understood that the stressed spring assembly 46 or 146 could be replaced by a stressed spring assembly of the type disclosed and claimed in U.S. Pat. No. 4,755,169, the disclosure of which is hereby incorporated by reference into the present specification. The stressed spring assembly of the patent combines the functions of the safety and the releasing member into one member which when moved from its safety storage position into its actuating position effects actuation by changing the locking surfaces effectively into cam surfaces.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. An autoinjector converted from an intramuscular to a subcutaneous mode of injection comprising housing means, medicament cartridge assembly means mounted within said housing means in a storage position for movement out of said storage position, cartridge moving means carried by said housing means for moving said medicament cartridge assembly means out of said storage position, said medicament cartridge assembly means including operatively rigid container means, a hypodermic needle, and medicament means disposed in a storage condition within said container means when said medicament cartridge assembly means is in said storage position operable when said medicament cartridge assembly means is moved out of said storage position to provide liquid medicament injectable through said hypodermic needle, said moving means including stressed spring assembly means operable to effect an intramuscular mode of injection by moving said hypodermic needle outwardly of said housing means into the muscle tissue at the injection site of a user and a major portion of said liquid medicament outwardly through said hypodermic needle into the muscle tissue of the user, said stressed spring assembly means including spring means, releasable means for releasably retaining said spring means in a stressed condition, and releasing means for releasing said releasable means in response to the performance of a predetermined manual actuating procedure which includes a digital actuation while holding said housing means in an operative relation with respect to the skin at the injection site of the user, which may be such as to cause no compression of the subcutaneous tissue under the skin, and subcutaneous mode means secured in a subcutaneous mode position for converting the mode of injection effected by said stressed spring assembly from said intramuscular mode of injection to a subcutaneous mode of injection in which said needle cannot extend substantially beyond subcutaneous tissue at the injection site of the user during the movement of said needle outwardly of said housing means and a major portion of the liquid medicament enters into the subcutaneous tissue of the user during the movement of said liquid medicament outwardly of said needle.

2. An autoinjector as defined in claim 1 wherein said releasing means includes a releasing member disposed in a storage position at a rearward end of said housing means so that a user grasping said housing means in one hand can extend the thumb of that hand over said releasing member, means mounting said releasing member for movement from said storage position into an actuating position during the predetermined manual actuating procedure including thumb pressure on said releasing member while the housing means is held in a non-subcutaneous tissue compressing operative position with respect to the skin at the injection site of the user, said releasable means being operable to release the spring means from its retained stressed condition in response to the movement of said releasing member into said actuating position.

3. An autoinjector as defined in claim 2 wherein said container means includes a cylindrical container having an open rearward end and a necked down forward end, said cartridge assembly means further including a hub assembly fixedly securing a rearward end of said needle with the necked down forward end of said container, a resilient sheath extending over said needle when said cartridge assembly means is in said storage position operable during an initial portion of said cartridge assembly means movement out of said storage position to be compressed within said housing means by the movement of said container carrying said needle outwardly of said housing means after having pierced said sheath and a piston slidably sealingly mounted in the rearward open end of said container operable during the initial portion of said cartridge assembly means movement out of said storage position to move with said container and to thereafter slidably sealingly move within said container to effect movement of the liquid medicament out of said needle after the movement of the needle has stopped.

4. An autoinjector as defined in claim 3 wherein said hub assembly includes a burstable seal disposed in a storage position within said hub assembly so as to seal said liquid medicament within said container out of contact with said needle, said burstable seal being burstable in response to the initial movement of said piston within said container.

5. An autoinjector as defined in claim 4 wherein said housing means defines an exterior configuration of a size approximately the same as that of a conventional fountain pen, said housing means including a housing body assembly of elongated generally cylindrical configuration having a needle extension end and an opposite end and a separate housing cap structure of elongated generally cylindrical configuration having an open end and an opposite closed end, an elongated clip having one end fixed to the exterior of said cap structure adjacent the closed end thereof so as to extend longitudinally therealong and a free end biased to engage with the exterior of said cap structure adjacent the open end thereof whereby said clip serves to secure said exterior housing within a pocket on the person of a user, means between said housing body assembly and said housing cap structure for detachably securing said separate housing cap structure in open ended telescopic relation with an opposite end portion of said housing body assembly so that the latter is secured together with said cap structure within such pocket by said clip, said housing cap structure covering said releasing member when said housing cap structure is secured to said housing body assembly so as to prevent thumb engagement thereof without said housing cap structure being detached from said housing body assembly thereby enabling said housing cap structure to serve the dual purposes of (1) facilitating the securement of the housing cap structure and body assembly with the user's pocket and (2) alleviating the likelihood of an unwanted movement of said hypodermic needle outwardly of said housing means and an unwanted movement of the liquid medicament outwardly of the hypodermic needle.

6. An autoinjector as defined in claim 5 wherein said stressed spring assembly means includes a safety member mounted in an exterior position extending from the opposite end of said housing body assembly for manual removal from said exterior position, said safety member having means for (1) preventing movement of said releasing member into said actuating position when said safety member is in said exterior position and (2) enabling movement of said releasing member into said actuating position when said safety member is removed from said exterior position, said predetermined manual actuating procedure including a manual gripping of said safety member and removal thereof from said exterior position prior to the movement of said releasing member into said actuating position.

7. An autoinjector as defined in claim 6 wherein said forward housing structure defines a portion of said chamber containing said medicament cartridge assembly, said rearward housing member and said releasing member forming parts of said releasable stressed spring assembly means, and means for securing a forward end portion of said rearward housing member with a rearward end portion of said forward housing so as to retain the medicament cartridge assembly means contained within the latter in cooperating relation with said releasable stressed spring assembly carried by said rearward housing member.

8. An autoinjector as defined in claim 7 wherein said releasable means comprises a collet member having a flanged forward end portion and a plurality of locking elements on a rearward end portion normally biased into a locking position and operable to be moved relatively toward one another against such bias into a releasing position, said locking elements including forwardly facing locking surfaces, said rearward housing member including rearwardly facing locking surface means disposed to be engaged by the forwardly facing locking surfaces of said locking elements when in said locking position, said spring means comprising a compression coil spring compressed between an interior rearwardly facing abutment surface on said rearward housing member and the flanged forward end portion of said collet, said releasing means comprising inclined surfaces on said locking elements and cooperating surface means on said tubular releasing member for engaging said inclined surfaces and moving said locking elements toward one another in response to the movement of said tubular releasing member from said storage position into said actuating position to thereby disengage the forwardly facing locking surfaces of said locking elements with said rearwardly facing locking surface means.

9. An autoinjector as defined in claim 8 wherein said releasing member includes a hollow rearward end portion of reduced diameter disposed rearwardly of said rearward housing member, said safety member including a forwardly extending pin portion disposed through the rearward end portion of said releasing member and between the locking elements of said collet when in said storage position so as to prevent relative movement of said locking elements toward one another out of the storage position thereof.

10. An autoinjector as defined in claim 9 wherein said subcutaneous mode means comprises an extension member secured in said subcutaneous mode position so as to extend from a forward end of said housing means out of which said needle is moved when said medicament cartridge assembly means is moved out of said storage position by said stressed spring assembly means.

11. An autoinjector as defined in claim 10 wherein said forward end of said housing means is defined by a forward housing member having an annular groove formed in an exterior periphery thereof within a forward end portion thereof, said extension member being secured in said subcutaneous mode position by a skirt extending rearwardly from said extension member over the annular groove in said forward housing member having an annular ridge of a size to snap into said groove in response to the movement of said skirt rearwardly over the forward end portion of said forward housing member.

12. An autoinjector as defined in claim 11 wherein said extension member includes a forward skin engaging surface spaced approximately 0.3 inches from a surface on the forward end of said forward housing member.

13. An autoinjector as defined in claim 1 wherein said subcutaneous means comprises an extension member secured in said subcutaneous mode position so as to extend from a forward end of said housing means out of which said needle is moved when said medicament cartridge assembly means is moved out of said storage position by said stressed spring assembly means.

14. An autoinjector as defined in claim 13 wherein said forward end of said housing means is defined by a forward housing member having an annular groove formed in an exterior periphery thereof within a forward end portion thereof, said extension member being secured in said subcutaneous mode position by a skirt extending rearwardly from said extension member over the annular groove in said forward housing member having an annular ridge of a size to snap into said groove in response to the movement of said skirt rearwardly over the forward end portion of said forward housing member.

15. An autoinjector as defined in claim 14 wherein said extension member includes a forward skin engaging surface spaced approximately 0.3 inches from a surface on the forward end of said forward housing member.

16. An autoinjector as defined in claim 3 wherein said subcutaneous mode means comprises an extension member secured in said subcutaneous mode position so as to extend from a forward end of said housing means out of which said needle is moved when said medicament cartridge assembly means is moved out of said storage position by said stressed spring assembly means.

17. An autoinjector as defined in claim 16 wherein said forward end of said housing means is defined by a forward housing member having an annular groove formed in an exterior periphery thereof within a forward end portion thereof, said extension member being secured in said subcutaneous mode position by a skirt extending rearwardly from said extension member over the annular groove in said forward housing member having an annular ridge of a size to snap into said groove in response to the movement of said skirt rearwardly over the forward end portion of said forward housing member.

18. An autoinjector as defined in claim 17 wherein said extension member includes a forward skin engaging surface spaced approximately 0.3 inches from a surface on the forward end of said forward housing member.

19. An autoinjector as defined in claim 1 wherein said container means comprises an open ended container mounted within said chamber of said housing body assembly for retention in the storage position thereof wherein a forward open end thereof is disposed at the needle extension end of said housing body assembly, said container having an elastomeric stopper at said forward end thereof and a piston slidably sealingly mounted within a rearward opened end portion thereof, a spacer extending rearwardly of said piston in cooperating relation with the stressed spring assembly, said liquid medicament and said hypodermic needle being mounted within said container between said stopper and said piston when in said storage position, said spacer and said piston being movable by said spring means from the storage position thereof to an extended position during which said hypodermic needle is moved through said stopper and into the tissue of the user and said liquid medicament is moved through said hypodermic needle into the tissue of the user.

20. An autoinjector as defined in claim 19 wherein said subcutaneous mode means comprises a separate collar secured on said spacer in a position to engage the rearward open end of said container so as to stop the movement of said piston in spaced relation to said stopper and said needle in a subcutaneous position prior to reaching a fully extended intramuscular position.

21. An autoinjector as defined in claim 2 wherein said container means comprises an open ended container mounted within said chamber of said housing -body assembly for retention in the storage position thereof wherein a forward open end thereof is disposed at the needle extension end of said housing body assembly, said container having an elastomeric stopper at said forward end thereof and a piston slidably sealingly mounted within a rearward opened end portion thereof, a spacer extending rearwardly of said piston in cooperating relation with the stressed spring assembly, said liquid medicament and said hypodermic needle being mounted within said container between said stopper and said piston when in said storage position, said spacer and said piston being movable by said spring means from the storage position thereof to an extended position during which said hypodermic needle is moved through said stopper and into the tissue of the user and said liquid medicament is moved through said hypodermic needle into the tissue of the user.

22. An autoinjector as defined in claim 21 wherein said subcutaneous mode means comprises a separate collar secured on said spacer in a position to engage the rearward open end of said container so as to stop the movement of said piston in spaced relation to said stopper and said needle in a subcutaneous position prior to reaching a fully extended intramuscular position.

* * * * *